(12) United States Patent
Segil et al.

(10) Patent No.: US 10,632,003 B2
(45) Date of Patent: Apr. 28, 2020

(54) SYSTEMS AND METHODS FOR POSTURAL CONTROL OF A MULTI-FUNCTION PROSTHESIS

(71) Applicant: The Regents of the University of Colorado, Denver, CO (US)

(72) Inventors: Jacob Segil, Boulder, CO (US); Richard Weir, Longmont, CO (US)

(73) Assignee: The Regents of the University of Colorado, Denver, CO (US)

(*) Notice: Subject to any disclaimer, the term of this patent is extended or adjusted under 35 U.S.C. 154(b) by 0 days.

(21) Appl. No.: 14/891,551

(22) PCT Filed: Jun. 2, 2014

(86) PCT No.: PCT/US2014/040569
§ 371 (c)(1),
(2) Date: Nov. 16, 2015

(87) PCT Pub. No.: WO2014/197401
PCT Pub. Date: Dec. 11, 2014

(65) Prior Publication Data
US 2016/0074181 A1    Mar. 17, 2016

Related U.S. Application Data

(60) Provisional application No. 61/830,504, filed on Jun. 3, 2013.

(51) Int. Cl.
*A61F 2/72* (2006.01)
*A61F 2/58* (2006.01)
(Continued)

(52) U.S. Cl.
CPC ............... *A61F 2/72* (2013.01); *A61F 2/583* (2013.01); *A61F 2002/704* (2013.01); *A61F 2002/7635* (2013.01)

(58) Field of Classification Search
CPC .......... A61F 2/70; A61F 2/72; A61F 2002/704
See application file for complete search history.

(56) References Cited

U.S. PATENT DOCUMENTS

| | | | | |
|---|---|---|---|---|
| 4,650,492 A | * | 3/1987 | Barkhordar | ............ A61F 2/583 250/231.19 |
| 5,888,213 A | * | 3/1999 | Sears | ....................... A61F 2/68 623/24 |

(Continued)

FOREIGN PATENT DOCUMENTS

WO    WO 2012-123693 A1    9/2012

OTHER PUBLICATIONS

Trachtenberg et al., Radio Frequency Identification—An Innovative Solution to Guide Dexterous Prosthetic Hands, 2011, IEEE, pp. 3511-3514.*

(Continued)

*Primary Examiner* — Bruce E Snow
*Assistant Examiner* — Melissa A Hoban

(57) ABSTRACT

Systems and methods for postural control of a multi-function prosthesis are provided. Various embodiments provide for a postural controller that use EMG signals to drive a point in a posture space and outputs continuously varying joint angles for a powered prosthetic hand. The postural controller can include an EMG signal processing unit to receive signals from electrodes for processing (e.g., band pass filtering, rectification, root mean square averaging, dynamic tuning, etc.). The processed EMG signals can then be combined or converted to produce a point in the postural control domain. The PC domain map defines the posture that corresponds to each PC cursor coordinate. This map can have limitless possible postures and limitless possible positions of the postures. The Joint Angle Transform converts the PC cursor coordinate into the joint angle array which is (Continued)

sent to the prosthetic hand thereby creating more natural movements.

11 Claims, 10 Drawing Sheets

(51) Int. Cl.
    *A61F 2/70*     (2006.01)
    *A61F 2/76*     (2006.01)

(56) References Cited

U.S. PATENT DOCUMENTS

| | | | |
|---|---|---|---|
| 8,915,871 B2* | 12/2014 | Einav | G06F 19/00 601/5 |
| 2004/0117034 A1* | 6/2004 | Weir | A61F 2/583 623/24 |
| 2006/0018516 A1* | 1/2006 | Masoud | G06K 9/00342 382/115 |
| 2006/0149337 A1* | 7/2006 | John | A61N 1/36082 607/45 |
| 2011/0264238 A1 | 10/2011 | van der Merwe et al. | |
| 2011/0307079 A1* | 12/2011 | Oweiss | A61B 5/048 623/27 |
| 2013/0053984 A1* | 2/2013 | Hunter | A61F 2/583 623/64 |
| 2013/0197671 A1* | 8/2013 | Johannes | A61F 2/583 623/64 |
| 2013/0253705 A1* | 9/2013 | Goldfarb | A61F 2/583 700/260 |
| 2013/0338540 A1* | 12/2013 | Hargrove | A61B 5/11 600/595 |
| 2015/0178988 A1* | 6/2015 | Montserrat Mora | G06T 13/40 345/420 |

OTHER PUBLICATIONS

International Application No. PCT/US2014/040569, International Search Report & Written Opinion, 10 pages, dated Dec. 19, 2014.

G. C. Matrone et al. "Principal components analysis based control of a multi-dof underactuated prosthetic hand," Journal of neuroengineering and rehabilitation, vol. 7, No. 1, p. 16, 2010. DOI:10.1186/1743-0003-7-16.

G. Matrone et al. "Two-channel real-time EMG control of a dexterous hand prosthesis," in Neural Engineering (NER), 2011 5th International IEEE/EMBS Conference on, Apr. 2011, pp. 554-557. DOI:10.1109/NER.2011.5910608.

G. C. Matrone et al. "Real-time myoelectric control of a multi-fingered hand prosthesis using principal components analysis," Journal of NeuroEngineering and Rehabilitation, vol. 9, No. 1, p. 40, 2012. DOI:10.1186/1743-0003-9-40.

* cited by examiner

SYSTEMS AND METHODS FOR POSTURAL CONTROL OF A MULTI-FUNCTION PROSTHESIS

CROSS-REFERENCE TO RELATED APPLICATIONS

This application is a national phase of International Application No. PCT/US2014/040569 filed on Jun. 2, 2014, which claims priority to U.S. Provisional Patent Application No. 61/830,504 filed Jun. 3, 2013, both of which are incorporated herein by reference in their entirety for all purposes.

TECHNICAL FIELD

Various embodiments of the present invention generally relate to systems and methods for postural control. More specifically, some embodiments of the present invention relate to myoelectric postural controllers for multi-function prostheses.

BACKGROUND

A prosthesis is an artificial device that is used to replace a missing body part (e.g., a limb). For example, a transhumeral prosthesis is an artificial limb that replaces an arm missing above the elbow. While prosthetic devices have been in use for centuries, early prosthetic devices were quite basic. With the advent of new materials, processors, and electronics, prosthetic devices have become more interactive. For example, a myoelectric prosthesis uses electromyographic (EMG) signals from voluntarily contracted muscles within a person's residual limb to control the movements of the prosthesis. The electromyographic signals may be used for elbow flexion/extension, wrist supination/pronation (rotation), hand opening/closing of the fingers, or other functions. Unfortunately, these traditional designs allow for only a single posture or for the user to cycle through a small number of pre-defined postures.

SUMMARY

Systems and methods are described for postural control of a multi-function prosthesis. A multi-function prosthesis is a prosthetic device with multiple actuators capable of generating multiple postures. In some embodiments, a prosthetic device can include a set of electrodes, an EMG signal processing module, a set of actuators, a postural controller, a feedback controller, actuators (e.g., two or more actuators), sensors (e.g., pressure sensors, accelerometers, encoders, etc.) and/or other components. The set of electrodes can be used to monitor muscle contractions and generate electromyographic (EMG) signals. The set of electrodes can include surface electrodes placed on the outside of the user's skin. In some cases, the set of electrodes may include electrodes implanted within the muscles of the user. The EMG processing module can receive the EMG signals and generate processed EMG signals. The set of actuators can control joint angles of the prosthetic device.

The postural controller can receive the processed EMG signals and determine a desired set of joint angles defining a desired posture by controlling a point in a postural control space. The postural control space can be defined through graphical user interface by an anaplastologist or pre-set defaults. In some embodiments, the postural controller can include a conversion module and a joint angle transformer.

The conversion module can be configured to receive processed EMG signals. The conversion module can then map the processed EMG signals to a point in the postural control space, wherein the point in the postural control space lies between two postures. For example, in some embodiments, the conversion module can use a vector summation algorithm to map the processed EMG signals to a point in the postural control space. The joint angle transformer can be configured to transform the point in the postural control space into a set of desired joint angles by morphing the joint angles of the two postures.

The feedback controller can generate control signals to set the joint angles of the prosthetic device using the set of actuators. The prosthetic device can also include one or more pressure sensors, accelerometers, and/or encoders that generate signals that can be used by the feedback controller to generate control signals to set the joint angles of the prosthetic device.

Some embodiments provide for a processor-implemented method that includes monitoring, using an electrode array, signals indicative of a desired posture of a prosthetic device (e.g., prosthetic hand, a prosthetic arm, a prosthetic foot, or a prosthetic leg). The signals (e.g., EMG signals, peripheral neuron signals, computer generated signals, etc.) can be mapped, using a processor, to a point in a user specific posture space. In some embodiments, the signals can be mapped using vector summation. The posture of the prosthetic device can be set based on the point in the user specific posture space. In some embodiments, the signals can be filtered and/or dynamically tuned (e.g., using baseline reading from a user).

Embodiments of the present invention also include computer-readable storage media containing sets of instructions to cause one or more processors to perform the methods, variations of the methods, and other operations described herein.

Various embodiments include a postural controller. The postural controller may include one or more processor(s) and a memory having stored thereon a postural control space having a set of pre-selected postures each defining joint angles of a mechanical device. The postural controller may also include a conversion module configured to receive processed EMG signals (e.g., filtered, rectified, dynamically adjusted gains/thresholds/offsets, etc.) and map (e.g., using a vector summation algorithm) the processed EMG signals to a point in the postural control space using the one or more processor(s). The point in the postural control space may lie between two of the pre-selected postures. In some embodiments, the postural control space includes attractive regions or gravity wells around the pre-selected postures. These attractive regions allow a user of the mechanical device to get close to a posture and have the point in the postural control space continue towards the posture without continued effort by the user.

The joint angle transformer can use the one or more processors to transform the point in the postural control space into a set of desired joint angles. In some embodiments, the joint angle transformer may morph the joint angles into a linear combination of the two closest postures when the point lies between pre-selected postures in the postural control space. The postural controller may also include a feedback controller to generate control signals to cause a set of actuators to set the joint angles of the mechanical device. The feedback controller may use signals generated from various estimators or sensors (e.g., encoders, accelerometers, pressure sensors, etc.) to generate the control signals.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

BRIEF DESCRIPTION OF THE DRAWINGS

Embodiments of the present invention will be described and explained through the use of the accompanying drawings in which.

Figure 1:
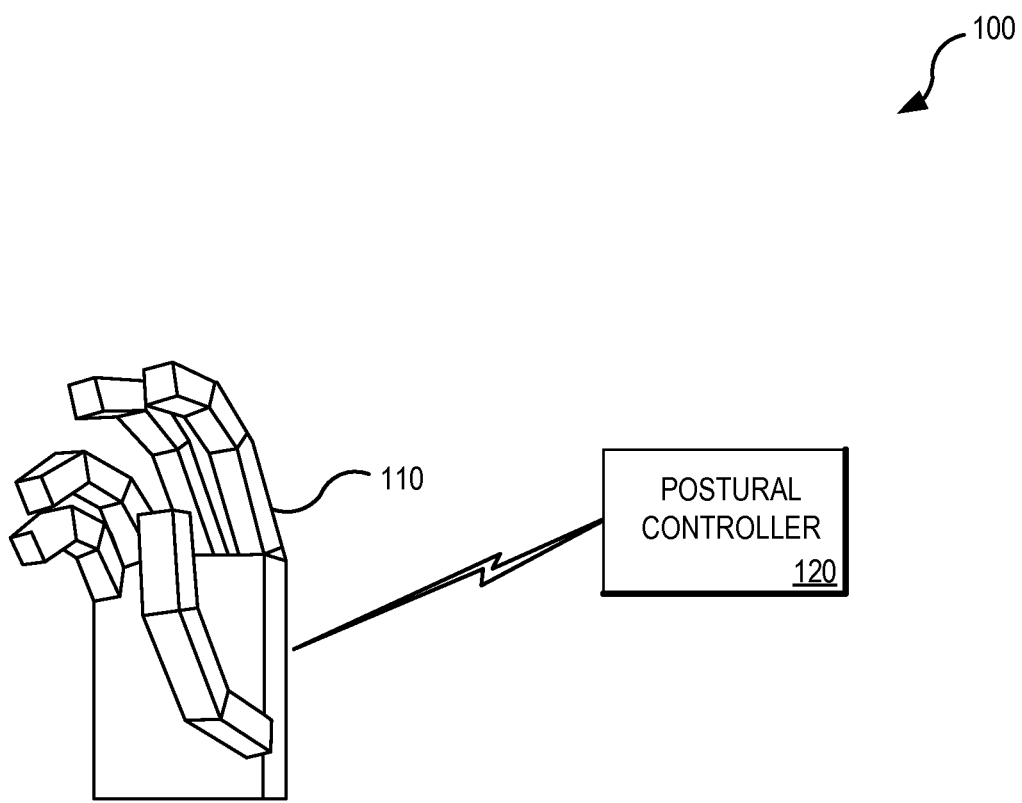
FIG. 1 illustrates an example of a prosthetic device in accordance with some embodiments of the present invention.

The drawings have not necessarily been drawn to scale. For example, the dimensions of some of the elements in the figures may be expanded or reduced to help improve the understanding of the embodiments of the present invention. Similarly, some components and/or operations may be separated into different blocks or combined into a single block for the purposes of discussion of some of the embodiments of the present invention. Moreover, while the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various embodiments of the present invention generally relate to systems and methods for postural control to command an array of joint angles for a prosthesis. More specifically, some embodiments of the present invention relate to myoelectric postural controllers for multi-function prostheses. Myoelectric control systems used by various embodiments of the present invention provide more functional and intuitive prosthetic limbs than traditional prosthetic devices. These techniques allow for a human-machine interface that deciphers user intent in real-time and allows for more intuitive and precise control of prosthetic devices. For example, while many traditional systems use a state-machine to cycle through a limited number of pre-selected postures in a specific order, various embodiments of the present invention provide for an unlimited (or almost unlimited) number of possible postures. In some embodiments, a user is able to continuously morph between postures providing for more biomimetic prosthetic devices.

The postural control techniques used by various embodiments of the present invention transform command or input signals (e.g., the EMG input signals) into an array of joint angles (i.e., a posture) using a transformation (e.g., a linear transformation) based on a kinematic coupling. The relative magnitude of each command signal modulates the contribution of each corresponding postural vector. In many embodiments, these techniques include a dimensionality augmentation step caused by the transform. For example, the transform may take a small number of input signals and produce a larger number of output signals. As a result, depending on the transform, some postures may not be reachable.

Some embodiments include an effective myoelectric interface to command a multi-function prosthetic hand into various grasps and postures. These embodiments can use custom Postural Control Domain (PC domain) that allows the subject to continuously morph advanced prosthetic hands into limitless number of postures. Some advantages of the systems and techniques disclosed herein include the following: 1) design of intuitive custom control spaces; 2) allows for transformation between all postures within PC domain without restriction as opposed to state machines which define a specific sequence which the hand posture can transform; 3) robust to real world scenarios like donning/doffing, electrode shift, sweat, etc. unlike pattern recognition systems; 4) does not require training of a classifier like pattern recognition systems; and 5) provides a more intuitive interface as compared to state machines.

Some embodiments include preferred regions (e.g., a gravity mapping) that create a 'soft' state machine like functionality that assists in the formation of specific functional postures. Unlike traditional state machines, the user can command the prosthetic hand into any number of alternate postures as desired without the use of a trigger command (i.e.—co-contraction EMG signal, etc.). Gravity mapping and other preferred region techniques enhance the ability of subjects to reach functional postures using a feedback control system. Tuning of the feedback control system can create unique virtual gravity wells specific to each subject.

Some embodiments use a Vector Summation Algorithm (VSA) that defines a specific transformation between EMG signals and the PC domain. Various cursor control schemes can also be used to augment the ability of subject to morph the hand into specific postures. The PC domain space can be designed with a limitless number of postures. Postures can be placed in any position in the PC domain and as a result, the position of the postures can be placed in order to create an intuitive controller. A joint angle transform can be used in some embodiments to create a continuously morphing joint angle array that negates the need for more advanced mathematical processes like classifiers in pattern recognition systems.

In the following description, for the purposes of explanation, numerous specific details are set forth in order to provide a thorough understanding of embodiments of the present invention. It will be apparent, however, to one skilled in the art that embodiments of the present invention may be practiced without some of these specific details. While, for convenience, embodiments of the present invention are often described with reference to prosthetic hands, embodiments of the present invention are equally applicable to various other types of prosthetic devices and other robotic applications. Similarly, while many of the descriptions relate to myoelectric control based on measured EMG signals, other types of command signals measured from the subject and/or generated from a computer interface may be used.

Moreover, the techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions that may be used to program a computer (or other electronic devices) to perform a process. The machine-readable medium may include, but is not limited to, floppy diskettes, optical discs, compact disc read-only memories (CD-ROMs), magneto-optical discs, ROMs, random access memories (RAMs), erasable programmable read-only memories (EPROMs), electrically erasable programmable read-only memories (EEPROMs), application-specific integrated circuits (ASICs), magnetic or optical cards, flash memory, or other type of media/machine-readable medium suitable for storing electronic instructions.

Terminology

Brief definitions of terms, abbreviations, and phrases used throughout this application are given below.

The terms "connected" or "coupled" and related terms are used in an operational sense and are not necessarily limited to a direct physical connection or coupling. Thus, for example, two devices may be coupled directly, or via one or more intermediary media or devices. As another example, devices may be coupled in such a way that information can be passed therebetween, while not sharing any physical connection with one another. Based on the disclosure provided herein, one of ordinary skill in the art will appreciate a variety of ways in which connection or coupling exists in accordance with the aforementioned definition.

The phrases "in some embodiments," "according to some embodiments," "in the embodiments shown," "in other embodiments," and the like generally mean the particular feature, structure, or characteristic following the phrase is included in at least one implementation of the present invention, and may be included in more than one implementation. In addition, such phrases do not necessarily refer to the same embodiments or different embodiments.

If the specification states a component or feature "may", "can", "could", or "might" be included or have a characteristic, that particular component or feature is not required to be included or have the characteristic.

The term "module" or "engine" refers broadly to general or specific-purpose hardware, software, or firmware (or any combination thereof) components. Modules and engines are typically functional components that can generate useful data or other output using specified input(s). A module or engine may or may not be self-contained. Depending upon implementation-specific or other considerations, the modules or engines may be centralized or functionally distributed. An application program (also called an "application") may include one or more modules and/or engines, or a module and/or engine can include one or more application programs.

General Description

FIG. 1 illustrates an example of a prosthetic device 100 in accordance with some embodiments of the present invention. As illustrated in FIG. 1, prosthetic hand 110 is controlled by postural controller 120. Postural controller 120 can receive control signals from a command interface (e.g., a myoelectric interface, a neural interface, a computer system, etc.) to command prosthetic hand 110 into various grasps and postures. In some embodiments, postural controller 120 can use a subject specific Postural Control Domain (PC domain) that allows a user to continuously morph prosthetic hand 110 into limitless number of postures. The PC domain includes a pre-specified number (e.g., 4, 8, 11, or more) of hand postures activated by the control signals. The PC domain is built upon an underlying set of vectors spanning the available control signals (e.g., from the EMG signals generated from a user's muscles). Prosthetic device 100 may include multiple PC domains having different postures customized or optimized for specific activities (e.g., sports activities, daily living activities, work activities, etc.) The user of prosthetic device 100 may be able to easily transfer from one PC domain to another (e.g., using an interface on prosthetic device 100).

A user of prosthetic device 100 has skeletal muscles that are composed of muscle fibers that can be volitionally controlled. A neural command causes the actin and myosin filaments within the myofibrils to ratchet along the length of the sarcomere and produce a muscle contraction. The flow of ions across the muscle cell membrane during the contraction creates electric potentials that can be measured using electrodes. This naturally occurring voltage produces a quasi-Gaussian distributed random noise electric field called the electromyogram. The EMG signal can be measured from the surface of the skin using surface electrodes and/or within the muscle fiber using intramuscular electrodes. The EMG signal is a composite, or superposition, of all of the electric potentials created within the electrode detection volume. The measured signal is generally monotonic and is somewhat proportional to the amount of muscle activity in the detection volume.

A myoelectric interface, as used in some embodiments, uses the muscles as sources of control of signals for generating the commands. The muscle contractions are measured using electrodes. The site on the body where a myoelectric electrode is placed to measure an EMG signal is referred to as a control site. The EMG signal can then be processed and used as a control signal to set postures of the prosthesis.

Figure 2:
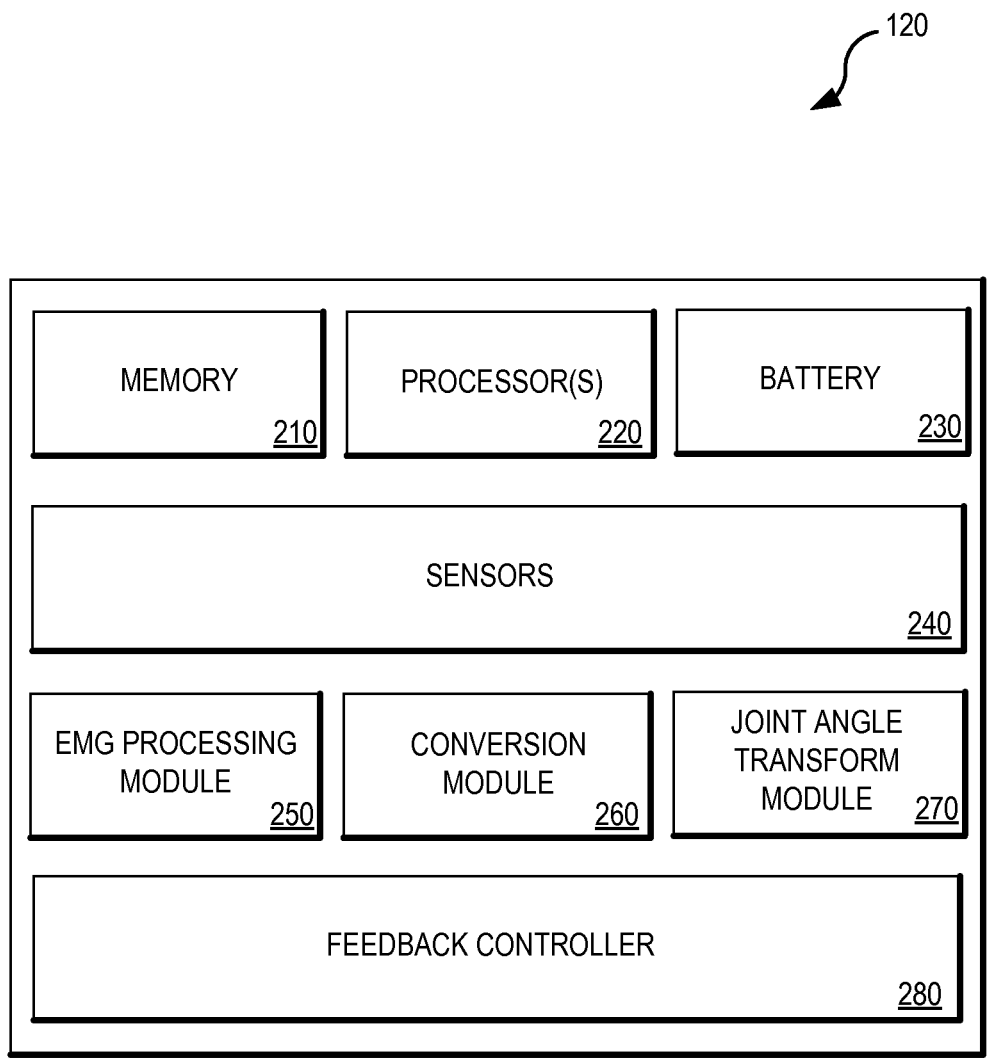
FIG. 2 illustrates an example of a set of components of a postural controller which may be used in accordance with one or more embodiments of the present invention.

FIG. 2 illustrates an example of a set of components of a postural controller 120 which may be used in accordance with one or more embodiments of the present invention. According to the embodiments shown in FIG. 2, postural controller 120 can include memory 210, one or more processors 220, battery 230, sensors 240, EMG processing module 250, conversion module 260, joint angle transform module 270, and feedback controller 280. Other embodiments of the present invention may include some, all, or none of these modules and components along with other modules, applications, and/or components. Still yet, some embodiments may incorporate two or more of these modules and components into a single module and/or associate a portion of the functionality of one or more of these modules with a different module. For example, in one embodiment, sensors 240 and EMG processing module 250 can be combined into a single module.

Memory 210 can be any device, mechanism, or populated data structure used for storing information. In accordance with some embodiments of the present invention, memory 210 can encompass any type of, but is not limited to, volatile memory, nonvolatile memory and dynamic memory. For example, memory 210 can be random access memory, memory storage devices, optical memory devices, media magnetic media, floppy disks, magnetic tapes, hard drives, SDRAM, RDRAM, DDR RAM, erasable programmable read-only memories (EPROMs), electrically erasable programmable read-only memories (EEPROMs), compact disks, DVDs, and/or the like. In accordance with some embodiments, memory 210 may include one or more disk drives, flash drives, one or more databases, one or more tables, one or more files, local cache memories, processor cache memories, relational databases, flat databases, and/or the like. In addition, those of ordinary skill in the art will appreciate many additional devices and techniques for storing information which can be used as memory 210.

Memory 210 may be used to store instructions for running one or more applications or modules on application processor(s) 220. For example, memory 210 could be used in one or more embodiments to house all or some of the instructions needed to execute the functionality of sensors 240, EMG processing module 250, conversion module 260, joint angle transform module 270, and/or feedback controller 280.

Processor(s) 220 are the main processors for controlling the prosthetic device. Processor(s) 220 can be communicably coupled with memory 210 and configured to run various user interfaces, manage communications between the controller and other components (e.g., external interfaces), and used for data gathering, data processing, and other applications stored on memory 210. Processor(s) 220 along with the other components (e.g., actuators) may be powered by battery 230 or other power source.

Sensors 240 can include an array of electrodes for measuring muscle contractions from a subject. The electrode array can include surface electrodes and/or intramuscular electrodes arranged about muscles designed to control the prosthetic device. For example, the electrode array could be placed around the circumference of a forearm in the case of a prosthetic hand. While this may be a natural choice in many situations, the electrode array may be placed in other locations. These electrodes can detect the electrical potential generated by an activated muscle. The signals can be analyzed to detect an activation level of the muscles since a stronger muscle contraction will result in a greater electrical potential. Sensors 240 may also include other types of sensors for measuring other physical quantities (e.g., force or pressure) or biological signals. For example, sensors 240 can include vision-based sensors, pressure sensors, and the like.

In some embodiments, four or more EMG signals may be acquired using electrode pairs (e.g., ProControl2 electrode pairs from Motion Control, Inc.) and self-adhesive Ag/AgCl snap electrode stickers (Noraxon USA, Inc.). The placement of the electrode will depend on the amputation, the remaining muscles, and/or any damage or limitations to the remaining muscles. In one test case, electrodes were placed on flexor digitorum superficialis, extensor digitorum, extensor carpi ulnaris, and flexor carpi ulnaris.

Unfortunately, the EMG signals are typically quite noisy. As such, EMG processing module 250 can be used to generate processed EMG signals. For example, the processed EMG signals may be the output after the signal has been sampled, band pass filtered, rectified, root mean square averaged, subject specific tuned, etc. For example, the measured raw EMG signals from the control sites may be amplified by the electrode and sent to a data acquisition device (e.g., NI USB-6008 National Instruments, Inc.). The raw analog EMG signal can be sampled at sufficient rates to capture the signal (e.g., at 1 kHz). The raw analog signal may be processed using band pass filters (e.g., 30-450 Hz), notch filters (e.g., at 60 Hz), rectification, smoothed (e.g., with a 200 ms moving average filter), and/or normalized individually to the signal input range of the data acquisition device. In some embodiments, a tuning process can be performed for each subject before the myoelectric sessions took place. The tuning process can include adjusting the gain and activation threshold for all EMG signals in order to produce the most comfortable control system for each subject. The gains can be adjusted to ensure that every task was achievable without overdue effort including co-contraction tasks (i.e. when postures lay far from the EMG signal axes in the PC domain). The activation thresholds were adjusted to negate quiescent EMG signals.

Figure 4:
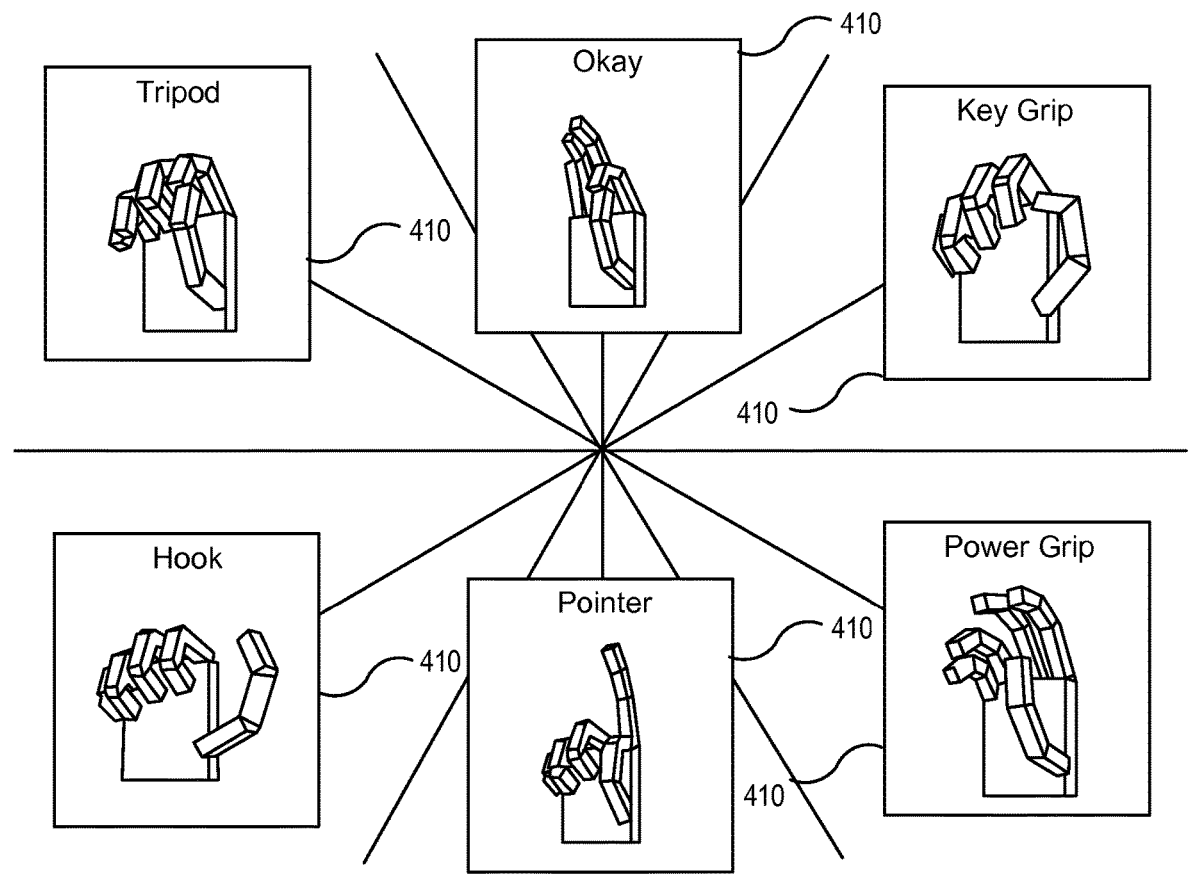
FIG. 4 illustrates an example of a postural domain in accordance with some embodiments of the present invention.

Conversion module 260 can convert the processed EMG signals to a postural control cursor coordinate (PCx, PCy) in the PC domain (see, e.g., FIG. 4). A variety of techniques may be used by conversion module 260. For example, in some embodiments a vector summation algorithm may be used. In other cases, a principal component of the EMG signals may be extracted and mapped to the PC domain. In accordance with some embodiments, conversion module 260 may use position cursor control techniques, velocity cursor control techniques, and/or force/acceleration cursor control techniques.

In accordance with various embodiments, the dimensionality of the PC domain can vary. The PC domain does not need to be a two dimensional plane. Some embodiments may use higher or lower dimensional space. For example, some embodiments may use a single dimension PC domain (i.e. a line). Other embodiments may use a three dimensional PC domain (i.e. a volume). In all cases, the subject would control a cursor (e.g., through a myoelectric interface or sensors) within the PC domain to control the posture of a hand or other mechanical device.

The vector summation algorithm (VSA) used by some embodiments of conversion module 260 is designed to interpret the 'snap-shot' of EMG activity (or other command signal) using a vector summation map. The vector summation map may be uniformly spaced in some embodiments. As an example, electrodes on the dorsal/ventral side of a limb (wrist extension/flexion) may correspond to the y-axis of the PC domain and electrodes on the medial/lateral side of the limb (ulnar/radial deviation) correspond to the x-axis of the PC domain (for a right-sided limb). The RMS EMG value determines the magnitude of each corresponding vector. The summation of all vectors produces a time varying resultant vector, $\vec{R}$.

Equation (1) below describes the calculation of $\vec{R}$ where $RMS_i$ is the RMS value of the $EMG_i$ signal, $\theta_i$ is the control site angle in the PC domain with respect to the x-axis, and N is the number of control sites. The direction of the resultant vector indicates the area in the forearm with the most EMG activity and the magnitude indicates the relative amount of EMG activity. In short, the VSA reduces the RMS EMG array into a single resultant vector ($\vec{R}$) that subsequently drives the time varying PC cursor coordinate ($PC_x$, $PC_y$)

$$\vec{R}(t) = \begin{bmatrix} R_x(t) \\ R_y(t) \end{bmatrix} = \sum_{i=1}^{N} \begin{bmatrix} \text{RMS}_i(t) \cos \theta_i \\ \text{RMS}_i(t) \sin \theta_i \end{bmatrix} \quad (1)$$

The resultant vector produced by the VSA ($\vec{R}$) controls the PC cursor coordinate ($PC_x$, $PC_y$) using a position or velocity cursor control scheme. The position control scheme interprets the resultant as a positional command vector (i.e.—units of distance). In the position cursor control scheme the end point of the resultant vector equals the time varying PC cursor coordinate described in equation (2).

$$\begin{bmatrix} PC_x(t) \\ PC_y(t) \end{bmatrix} = \begin{bmatrix} R_x(t) \\ R_y(t) \end{bmatrix} = \vec{R}(t) \quad (2)$$

The velocity cursor control scheme interprets the resultant as a velocity command vector (i.e.—units of distance/time). A discrete integration over time determines the cursor position as described in equation (3) where ($\vec{R}_j$) is the instantaneous resultant vector, $\Delta t_j$ is the loop time, $V_{gain}$ is the velocity gain, and j is the software loop count. The velocity gain adjusts the maximum allowable speed (i.e.—a speed limit). In practice, the magnitude of the resultant corresponds to the speed of the cursor and the direction of the resultant corresponds to the direction the cursor moves.

$$\begin{bmatrix} PC_x(t) \\ PC_y(t) \end{bmatrix} = V_{gain} * \sum_{j=1}^{J} (\vec{R}_j(t) * \Delta t_j) \quad (3)$$

Joint angle transform module 270 can use a joint angle transform to convert the PC cursor coordinate into the time varying joint angle array which is sent to the prosthetic hand thereby creating more natural movements. The joint angle transform can create a continuously morphing joint angle array that negates the need for more advanced mathematical processes like classifiers in pattern recognition systems. The joint angle array could command joints outside of the prosthetic hand. For example, the joint angle array could control the wrist angles (i.e.—supination/pronation, ulnar/radial deviation, and flexion/extension). In addition, various embodiments can control other limbs/joints (e.g., the elbow/shoulder and/or ankle/knee).

In some embodiments, joint angle transform module 270 can convert the PC cursor coordinate into a posture based on the postural map at a rate of 10 Hz. The postural map defines the number and location of the grasps available to the user in the PC domain. Points (targets) in the PC domain correspond to grasps. When the PC cursor coordinate equals the target, then the controller reproduces the grasp identically. As the PC cursor coordinate moves between two targets, the controller produces a linear combination of those two postures. A representative postural map is shown in FIG. 4.

The joint angle transform (JAT) may be a linear transform that converts the PC cursor coordinate into a joint angle array. The generalized equation defines the JAT (4) where ($PC_x$, $PC_y$) is the PC cursor coordinate, $JAT_{i,j}$ are the joint angles for the two closest postures to the PC cursor coordinate as determined by the postural map (i=1-6 for a 6 degree of freedom hand, j=1-2), and $\theta$ is the joint angle array. The posture mapping logic function (L, equation (5)) dynamically derives the appropriate JAT based on the PC domain map and produces a modified PC cursor coordinate ($PC_x'$, $PC_y'$) based in radial coordinates. The argument to L is the PC cursor coordinate ($PC_x$, $PC_y$) and a matrix which includes the coordinates of the targets as defined by the postural map (Postures). In real-time, L determines the closest two postures radially to the current PC cursor coordinate and thereby produces the JAT. In addition, L produces a modified PC cursor coordinate to distinguish the relative proximity of the cursor coordinate to the two closest postures. The modified PC cursor coordinate ensures that the controller morphs the hand posture as the cursor moves between two targets in the PC domain.

$$\theta = \begin{bmatrix} \theta_1 \\ \theta_2 \\ \theta_3 \\ \theta_4 \\ \theta_5 \\ \theta_6 \end{bmatrix} = JAT * \begin{bmatrix} PC_x(t) \\ PC_y(t) \end{bmatrix} = \quad (4)$$

$$\begin{bmatrix} JAT_{1,1}(PC_x, PC_y) & JAT_{1,2}(PC_x, PC_y) \\ JAT_{2,1}(PC_x, PC_y) & JAT_{2,2}(PC_x, PC_y) \\ JAT_{3,1}(PC_x, PC_y) & JAT_{3,2}(PC_x, PC_y) \\ JAT_{4,1}(PC_x, PC_y) & JAT_{4,2}(PC_x, PC_y) \\ JAT_{5,1}(PC_x, PC_y) & JAT_{5,2}(PC_x, PC_y) \\ JAT_{6,1}(PC_x, PC_y) & JAT_{6,2}(PC_x, PC_y) \end{bmatrix} \begin{bmatrix} PC_x'(t) \\ PC_y'(t) \end{bmatrix}$$

$$[PC_x', PC_y', JAT] = L(PC_x, PC_y, \text{Postures}) \quad (5)$$

This novel algorithm for a postural controller includes many customizable features (number of electrodes, cursor control schemes, potential field designs, postural map designs, etc.).

Feedback controller 280 can receive measurements (or estimates) of the current position, velocity, and/or accelerations of the prosthetic hand. Using this information, control signals can be generated (e.g., using a PI, PID, fuzzy logic, nonlinear, continuous, discrete, or adaptive controller) to control the actuators resulting in the movement of the hand between positions. Postural controller 120 can be used in different control modalities (other than position) depending on the hardware it is controlling. If the proper hardware sensors are available, the postural controller can be used in a position, velocity, force, or impedance control modality. The inputs from these sensors can be used in designing feedback controller 280.

Figure 3:
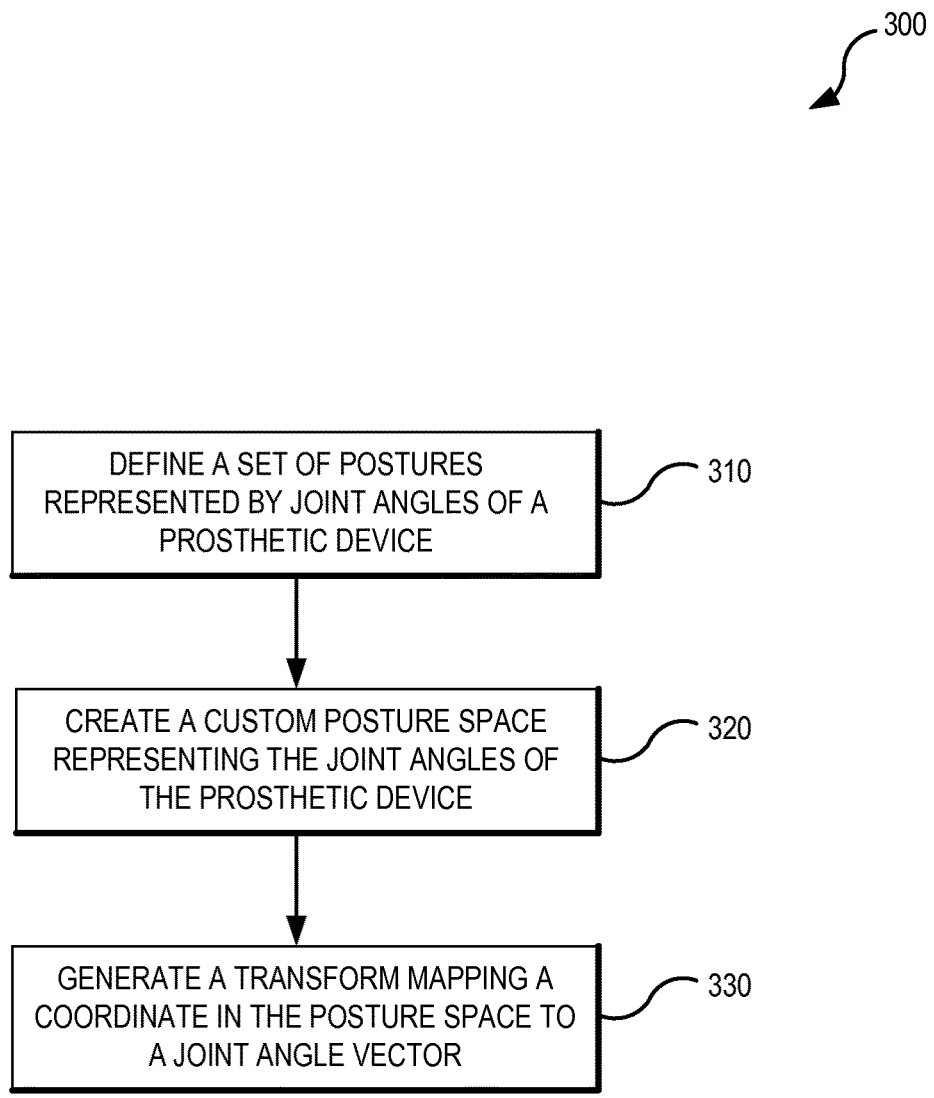
FIG. 3 is a flowchart illustrating an example of a set of operations for generating a custom transform in accordance with various embodiments of the present invention.
Figure 10:
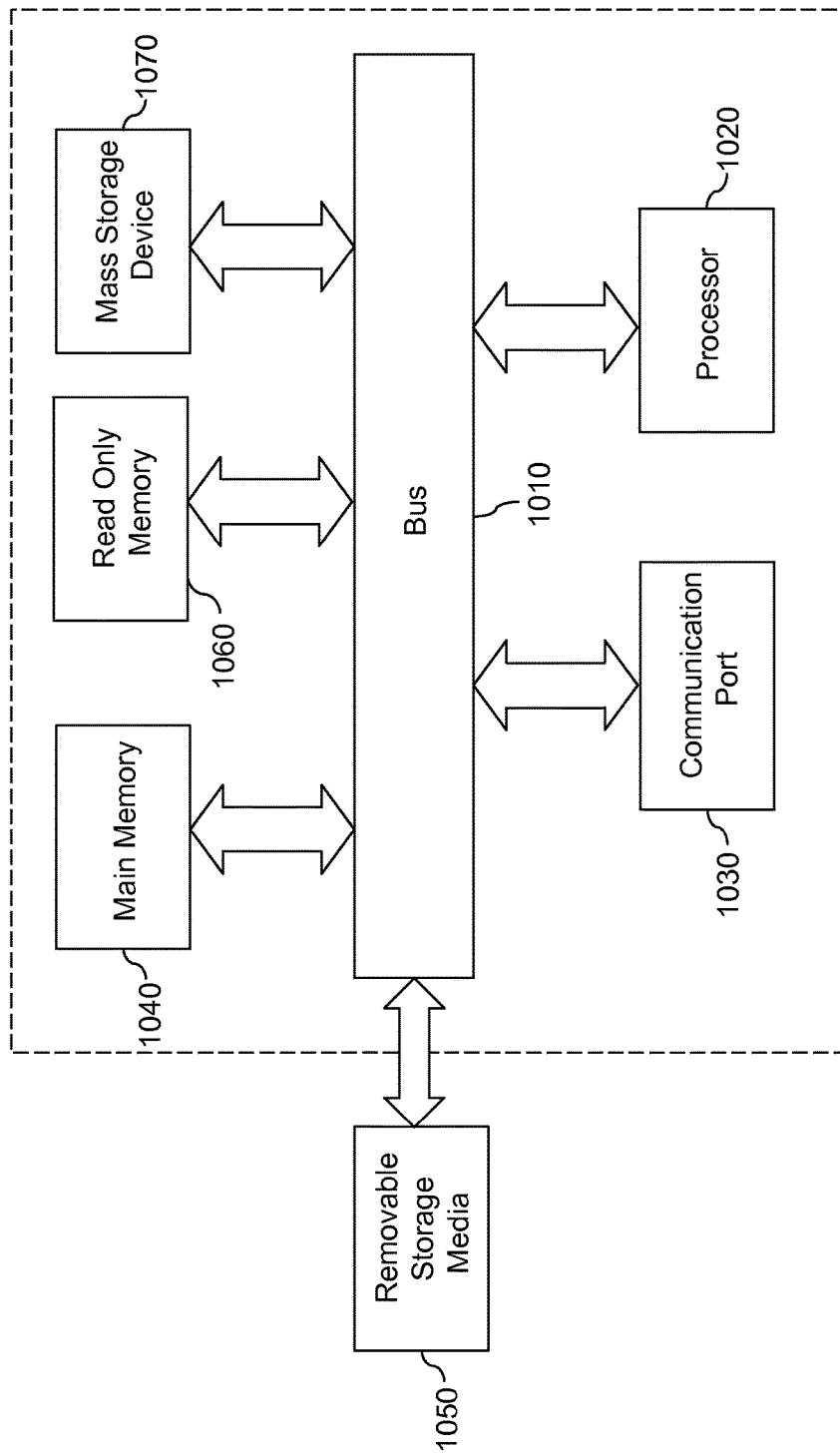
FIG. 10 illustrates an example of a computer system with which some embodiments of the present invention may be utilized.

FIG. 3 is a flowchart illustrating an example of a set of operations 300 for generating a subject specific transform in accordance with various embodiments of the present invention. The operations illustrated in FIG. 3 may be performed by a processor, computer (e.g., as illustrated in FIG. 10), or other device. As illustrated in FIG. 3, defining operation 310 can define a set postures (see, e.g., 410 in FIG. 4) represented by joint angles of a prosthetic device. The postures may be selected (e.g., using a graphical user interface) and possibly even customized to an individual user. The postures correspond to the information needed to set the posture of the prosthetic device (e.g., a set of joint angles).

Once the postures have been defined or selected, the posture space can be created in representation operation 320 by defining the relative orientation of the set of postures within the PC domain. The arrangement or relative orientation of the postures within the postural control space (see, e.g., FIG. 4) may be set by a user who desires certain morphed, intermediate, or blended postures to perform desired activities. In other cases, a user may simply specify the desired postures and then the system may determine the placement of the postures within the posture space. The arrangement of the posture space may be selected so as to balance the ability of the user with the complexity of the arrangement. A postural space with fewer number of postures that are spaced further apart in the posture space is an easier interface for the user and vice versa. Typically, the most commonly used postures like tripod, key grip, and power grip are arranged in the posture space so that they are most easily reproduced for the user. Also, it is recommended that the postures are arranged in the posture space in an intuitive manner with respect to the EMG axes so that the original neural command is reproduced as accurately as possible. For example, the EMG signal from flexor digitorum should be mapped towards tripod grip since activity in flexor digitorum indicates the flexion of the digits in a physiologically intact hand.

Generation operation 330 generates a transform mapping a coordinate in the posture space to a joint angle vector. In accordance with some embodiments, a transform mapping may include a single line of linear algebra as defined by equation 4. The joint angle transform may be a two column matrix where the two columns are made up of the joint angles of the two nearest postures in the posture space. At any moment in time, the columns of the JAT include two columns of Table 1 depending on the two nearest target postures. A novel aspect of this postural control scheme is that the JAT is spatially dependent (i.e.—the columns of the JAT change depending on the PC cursor coordinate). For example, when the point in the posture space is between lateral prehension (LP) and tip prehension (TP) then the JAT equals the following matrix.

$$JAT = \begin{bmatrix} 20 & 90 \\ 90 & 65 \\ 70 & 70 \\ 80 & 0 \\ 80 & 0 \\ 80 & 0 \end{bmatrix}$$

TABLE 1

|  | LP | TP | PP | HK | PT | CP | HF |
|---|---|---|---|---|---|---|---|
| Thumb Rotation (°) | 20 | 90 | 90 | 0 | 0 | 90 | 0 |
| Thumb Flexion (°) | 90 | 65 | 65 | 90 | 90 | 65 | 0 |
| Index Flexion (°) | 70 | 70 | 70 | 70 | 0 | 45 | 0 |
| Middle Flexion (°) | 80 | 0 | 80 | 80 | 80 | 55 | 0 |
| Ring Flexion (°) | 80 | 0 | 80 | 80 | 80 | 65 | 0 |
| Index Flexion (°) | 80 | 0 | 80 | 80 | 80 | 65 | 0 |

FIG. 4 illustrates an example of a postural domain (i.e., the PC domain) in accordance with some embodiments of the present invention. By placing two postures next to one another, when a cursor falls between the two postures, a blended or morphed posture can be created which is a combination of the two postures. In addition, the placement of the postures within the posture space can be customized to maximize the intuitiveness of the posture space for each specific subject. While six postures are illustrated in FIG. 4, other embodiments may allow more or less postures within the postural domain.

The lines illustrated in FIG. 4 indicate the direction of action for each of the control signals. In this example, twelve input signals are mapped in a radial fashion about the origin. Experimental results have shown that three input signals arranged in a radial fashion were equally as effective as four and twelve input signal. In a clinical setting, it may be beneficial to reduce the number of input signals (i.e. number of electrodes) and therefore three electrodes mapped in a radial fashion is recommended in some cases. Less input signals (i.e.—when the lines become further apart) requires the user to manipulate multiple control signals (i.e.—a co-contraction when using EMG input signals) in order to reach the space between the lines. Once the PC domain has been defined, a transform can be created which maps coordinates in the posture space to a joint angle vector (or array).

Figure 5:
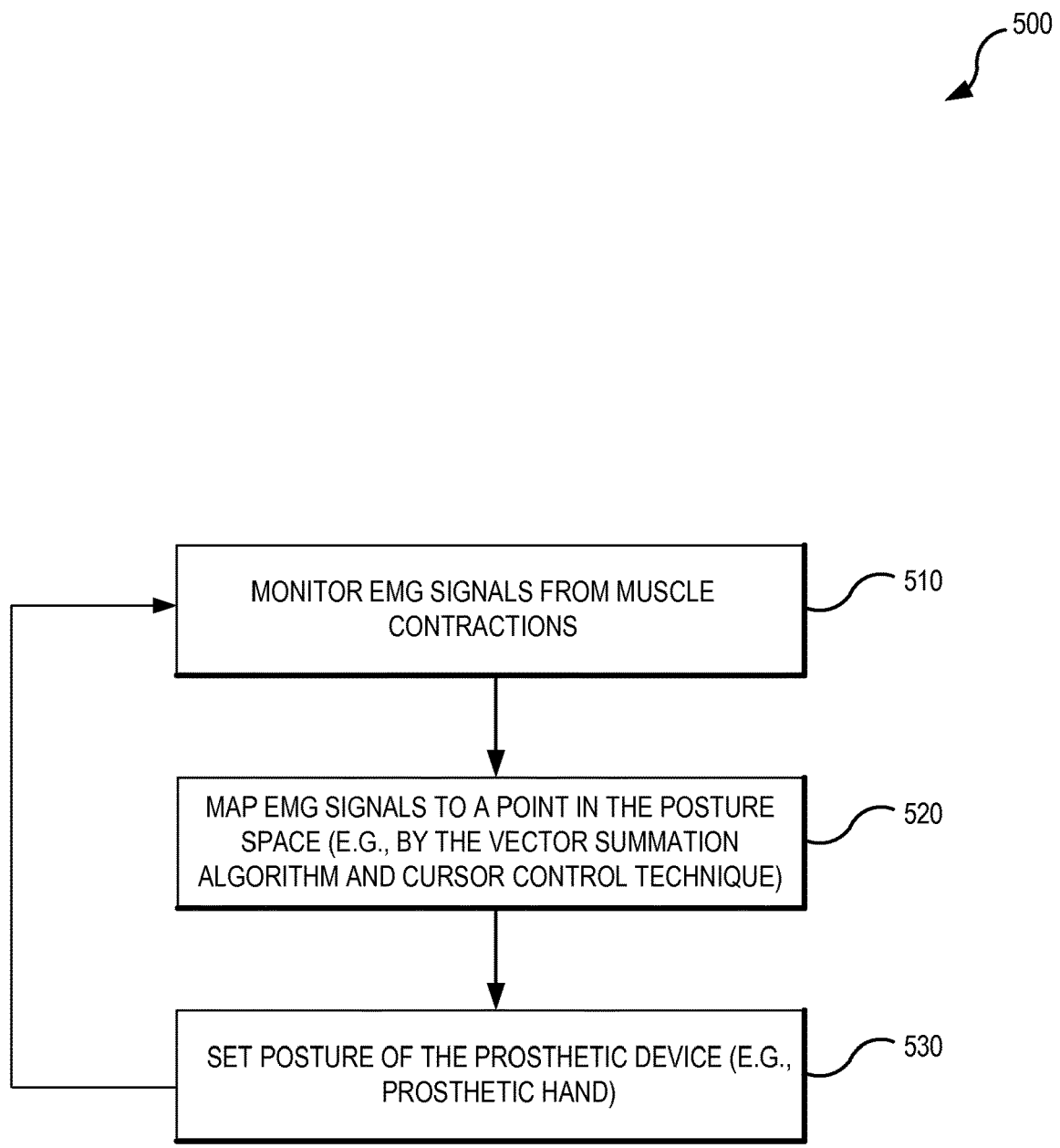
FIG. 5 is a flowchart illustrating an example of a set of operations for controlling a prosthetic device in accordance with one or more embodiments of the present invention.

FIG. 5 is a flowchart illustrating an example of a set of operations 500 for controlling a prosthetic device in accordance with one or more embodiments of the present invention. The operations illustrated in FIG. 5 may be performed by various components and devices, such as, but not limited to, prosthetic device 110, processor 220, sensors 240, conversion module 260, feedback controller 280, and/or other devices or components. Monitoring operation 510 monitors signals from muscle contractions. As discussed above, the signals may be processed (e.g., using band pass filters, statistical processing, sampling, etc.).

Mapping operation 520 maps the signals to a point in the posture space (e.g., by the vector summation algorithm). Mapping operation 520, for example, may use conversion module 260 to convert the processed EMG signals to a postural control cursor coordinate (e.g., (PCx, PCy)) in the PC domain. The coordinate in the PC domain corresponds to the posture, or blended posture, desired by the individual. Setting operation 530 sets the posture of the prosthetic device to the corresponding posture as selected by the point in the posture space as the process repeats. Setting operation may use a joint angle transform to map the point in the posture space to the physical settings (e.g., joint angles) needed to set the posture. Then, a controller can be used to set the posture of the prosthetic device.

Figure 6:
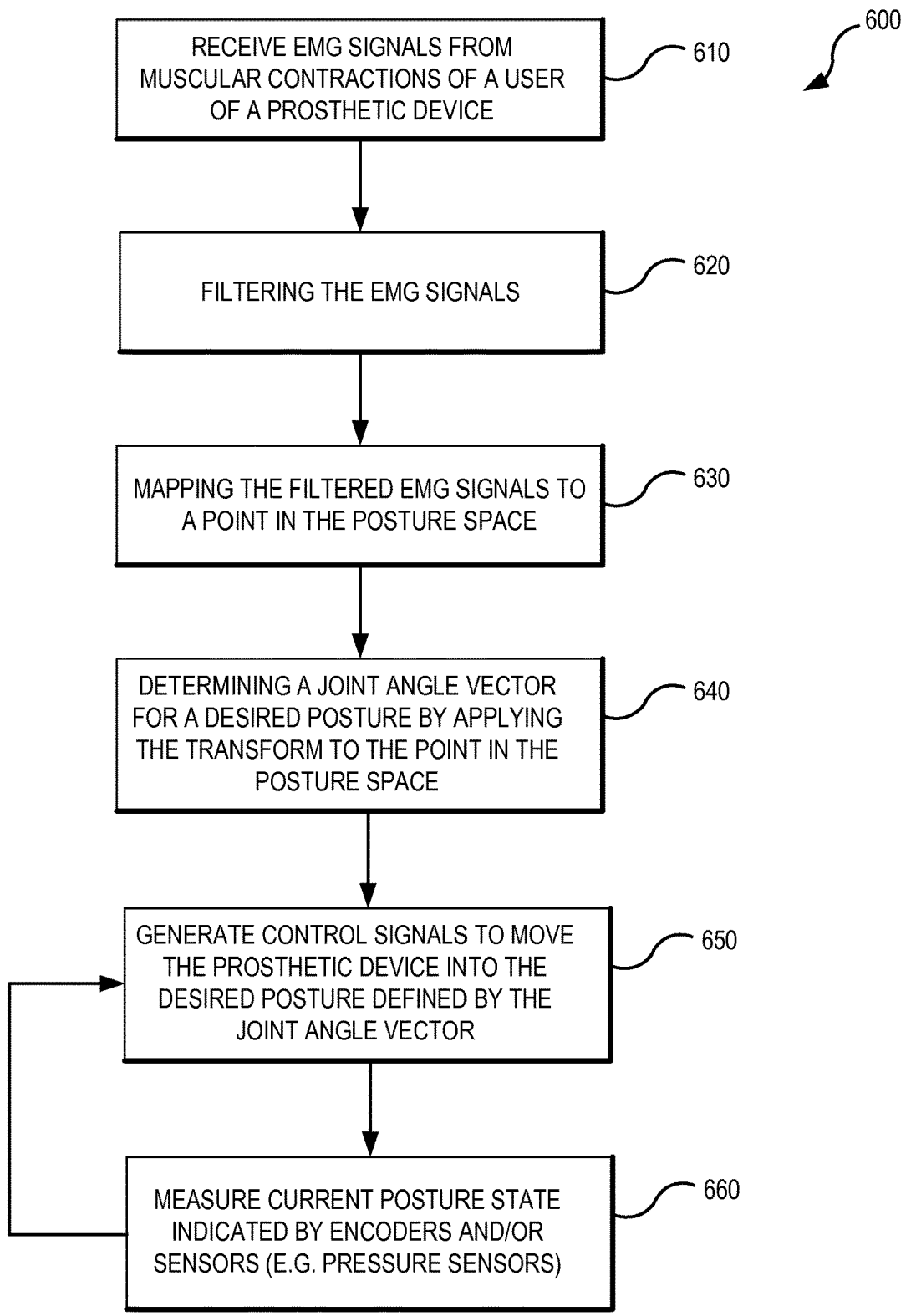
FIG. 6 is a flowchart illustrating an example of a set of operations for generating control signals for controlling the prosthetic device in accordance with various embodiments of the present invention.

FIG. 6 is a flowchart illustrating an example of a set of operations 600 for generating control signals for controlling the prosthetic device in accordance with various embodiments of the present invention. The operations illustrated in FIG. 6 may be performed by various components and devices, such as, but not limited to, prosthetic device 110, postural controller 120, processor 220, sensors 240, EMG processing module 250, conversion module 260, joint angle transform module 270, feedback controller 280, and/or other devices or components. During receiving operation 610 a set of EMG signals are received identifying muscular contractions of a user of a prosthetic device. The EMG signals represent the contractions of the musculature of the individual and accordingly, their intent to set the posture of the prosthetic device.

Filtering operation 620 filters the signals which are then mapped to a point in the posture space using mapping operation 630. This point can then be used to determine a joint angle vector (e.g., by applying a joint angle transform to the point) for the prosthetic device during determination operation 640. The joint angle vector specifies the positions of the joints of the prosthetic device. Once the joint angle vector has been determined, control operation 650 generates the control signals to move the prosthetic device into the desired posture defined by the joint angle vector. Measurement operation 660 measures the current posture state using encoders and/or other sensors. This information is fed back to the controller and used during control operation 650 to generate the control signals to move the prosthetic device into the desired posture defined by the joint angle vector.

Figure 7:
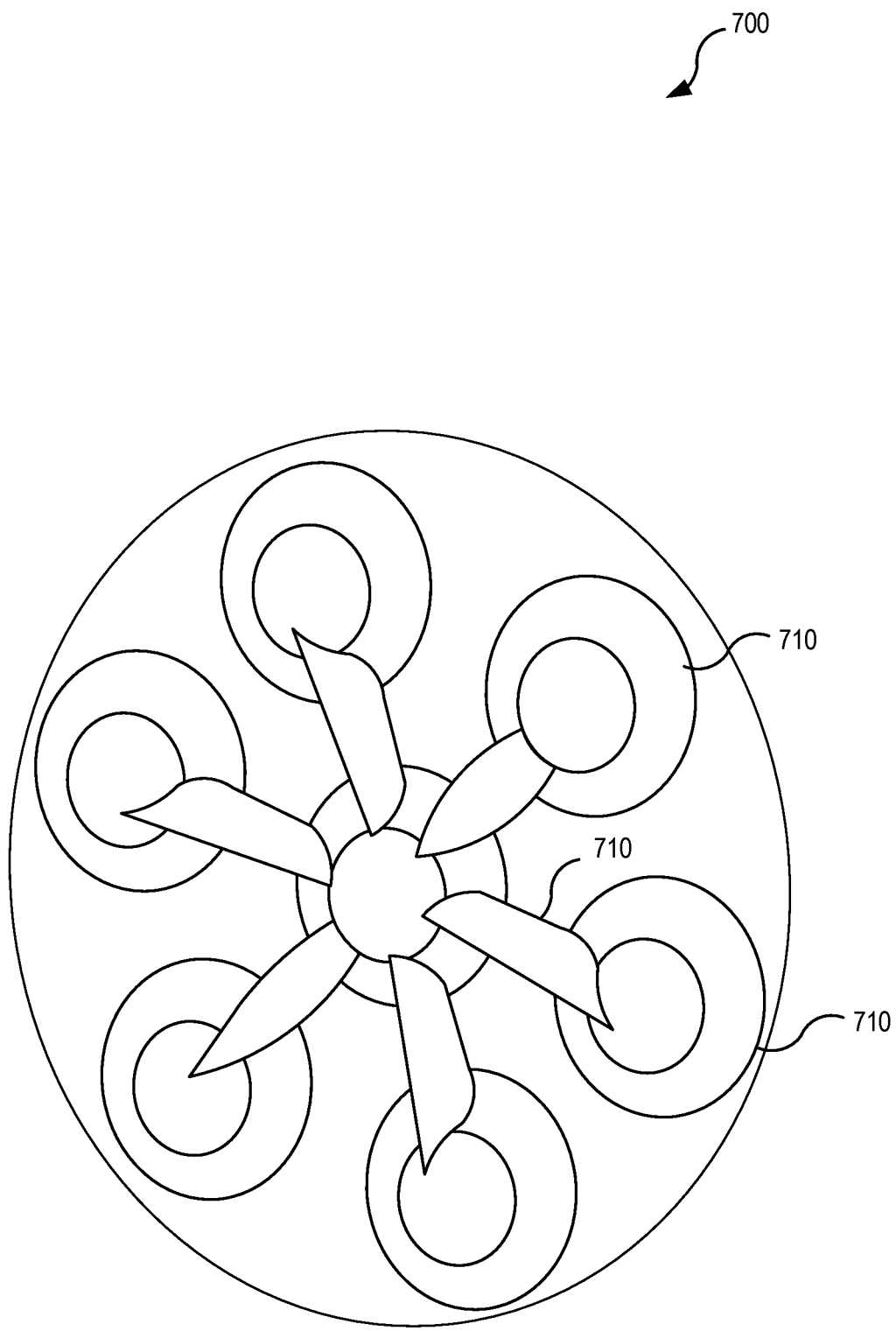
FIG. 7 illustrates an example of gravity wells which may be used with some embodiments of the present invention.

FIG. 7 illustrates an example 700 of soft attractors or gravity wells 710 which may be used with some embodiments of the present invention. Gravity wells 710 provide preferred regions (e.g., a gravity mapping) that create a 'soft' state machine like functionality that assists in the formation of specific functional postures. As the EMG signals are mapped to a point in the posture space, if the point falls within the gravity well, the prosthetic device will tend toward (or be attracted to) the posture associated with the gravity well. Unlike traditional state machines, however, the user can command the prosthetic hand into any number of alternate postures as desired. Gravity mapping enhances ability of the subjects to reach functional postures using a feedback control system. Tuning of feedback control system can create unique virtual gravity wells specific to each subject.

In some embodiments, for example, the gravity wells preferentially attract the cursor coordinate to certain regions in the PC domain using a position feedback loop (e.g., with a proportional-derivative controller). Similarly, the gravity wells could be gravity hills which repel the cursor coordinate from certain regions in the PC domain using a position feedback loop. The purpose of the potential field (that includes gravity wells/hills) is to augment the ability of the user to perform functional grasps using the postural controller. The potential field consists of potential augmentations surrounding the target positions and potential wedges emanating from the origin to the targets. The feedback controller forces the cursor toward the areas of lowest potential (i.e.—the bottom of the wells and wedges) and away from areas with highest potential. All parameters of the potential field (diameter of the wells/hills, width of the wedges, and depth of wells/hills and wedges) can be adjusted in order to best aid the user in performing functional grasps. In effect, the potential field adds a third dimension to the PC domain. The design of the potential fields can use various geometries such as only wells, only wedges, both wells/wedges, or other. The sequential processing of the resultant vector by the cursor control scheme and then the potential field produces a PC cursor coordinate ($PC_x$, $PC_y$) which the JAT converts into a hand posture.

Figure 8:
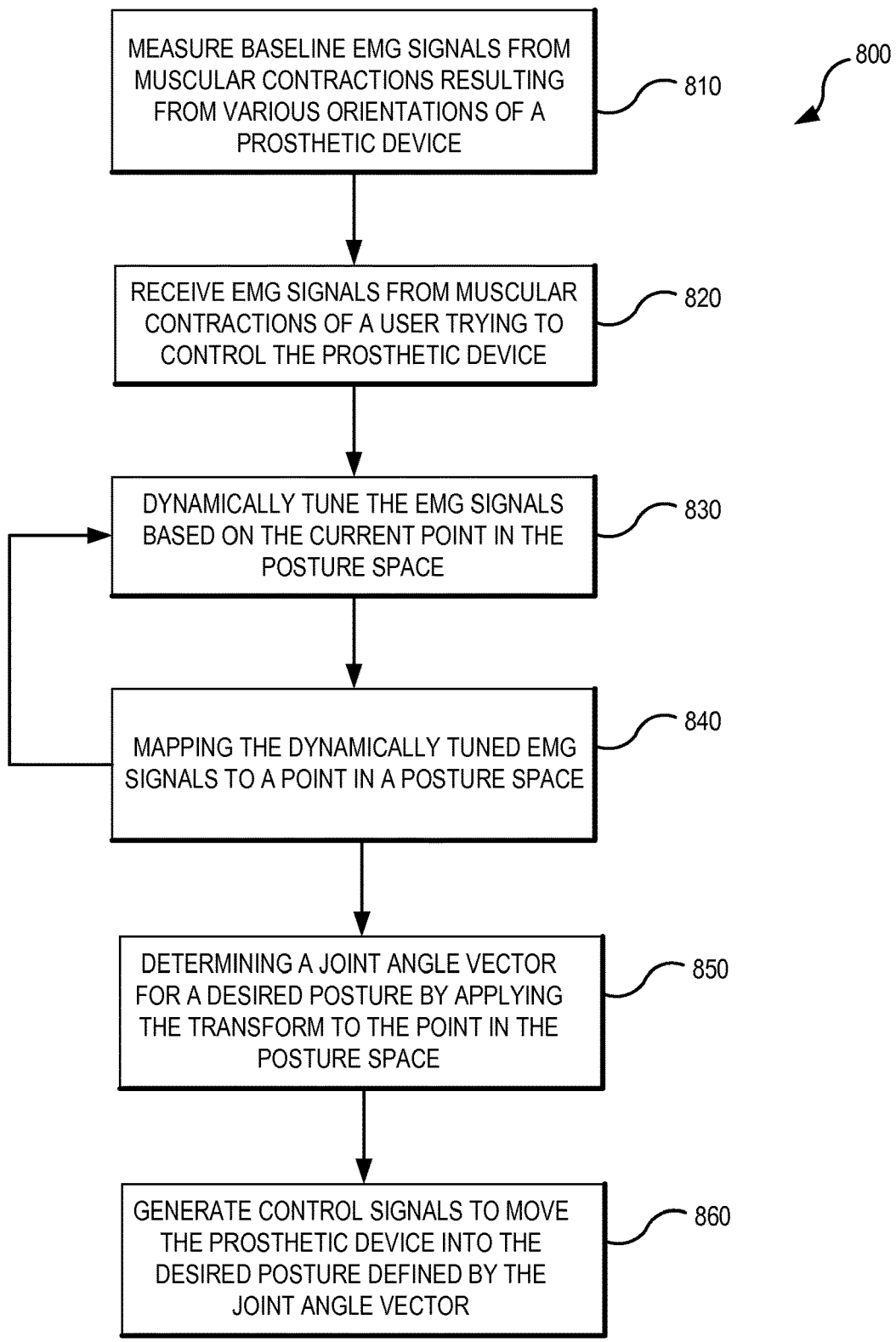
FIG. 8 is a flowchart illustrating an example of a set of operations for generating control signals for the prosthetic device using dynamically tuned EMG signals in accordance with one or more embodiments of the present invention.

FIG. 8 is a flowchart illustrating an example of a set of operations 800 for generating control signals for the prosthetic device using dynamically tuned EMG signals in accordance with one or more embodiments of the present invention. The operations illustrated in FIG. 8 may be performed by various components and devices, such as, but not limited to, prosthetic device 110, postural controller 120, processor 220, sensors 240, EMG processing module 250, conversion module 260, joint angle transform module 270, feedback controller 280, and/or other devices or components. The dynamic tuning techniques illustrated in FIG. 8 may be applied in order to compensate for co-activity within the musculature especially for persons with limb loss. One advantage of these dynamically tuned EMG signal techniques is that the prosthetic device produces more stable grasps and the controller is more robust to limb position affects since involuntary EMG activity is ignored.

As illustrated in FIG. 8, measurement operation 810 measure the baseline EMG signals from muscular contractions performed in different orientations of the prosthetic device. These measurements may be done once, periodically, or with every movement of the prosthetic device. As a result, in some embodiments, the baseline may change over time depending one when subsequent measurements are recorded. During receiving operation 820 a live set of EMG signals are received identifying muscular contractions of a user trying to set a posture of a prosthetic device. The EMG signals represent the contractions of the musculature of the individual and accordingly, their intent to set the posture of the prosthetic device.

Tuning operation 830 adjusts the EMG signals according to the current point in the posture space. These adjustments may be based on the baseline measurements recorded in measurement operation 810. The dynamically tuned EMG signals may then be mapped to a point in the posture space using mapping operation 840. This information can be fed back to tuning operation 830. The dynamic tuning algorithm is spatially dependent. When the point in the posture space crosses a certain spatial threshold the EMG gains may be adjusted in real time. Therefore, the point in the posture space must be feedback to the dynamic tuning block in order to adjust the EMG gains appropriately.

Determination operation 850 uses this point in the posture space to determine a joint angle vector (e.g., by applying a joint angle transform to the point) for the prosthetic device. The joint angle vector specifies the positions of the joints of the prosthetic device. Once the joint angle vector has been determined, control operation 860 generates the control signals to move the prosthetic device into the desired posture defined by the joint angle vector. In accordance with various embodiments, the control signals generated by control operation 860 may be based on the desired joint angle vector and measured (or estimated) states of the prosthetic device.

Figure 9:
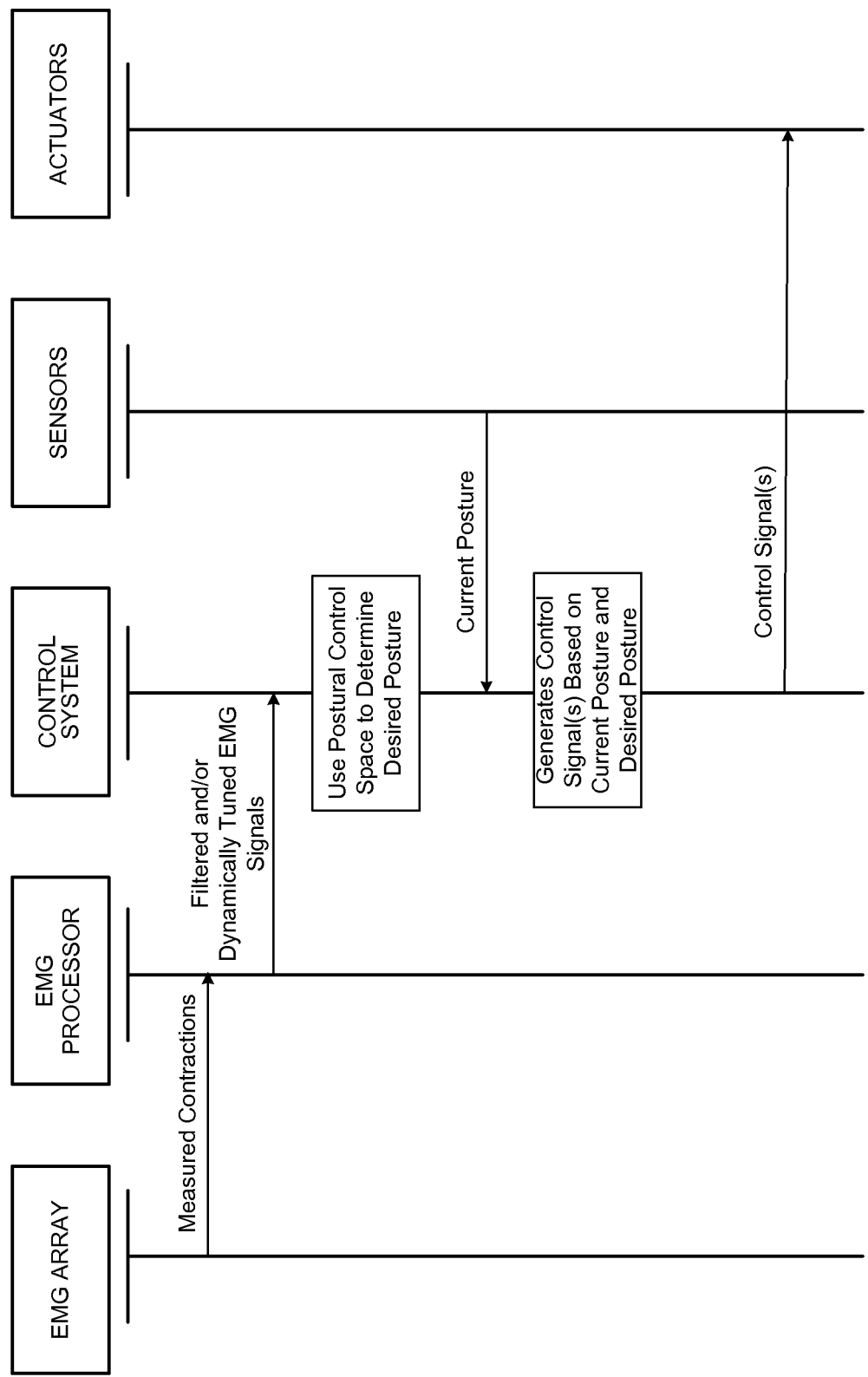
FIG. 9 is a sequence diagram illustrating a set of communications between various components of a prosthetic device in accordance with various embodiments of the present invention.

FIG. 9 is a sequence diagram illustrating a set of communications between various components of a prosthetic device in accordance with various embodiments of the present invention. As illustrated in FIG. 9, an EMG array measures contractions of muscles from a user. These EMG signals are processed by an EMG processor. For example, the EMG processor may filter, rectify, average, dynamically tune, etc. the EMG signals. The processed EMG signals are sent to the control system which uses a postural control space (i.e., the PC domain) to determine the desired posture of the prosthetic device. Various sensors can be used to determine the current posture of the prosthetic device. This information can be used by the control system to generate control signals to command the actuators of the prosthetic device to set the desired posture.

Various embodiments of the techniques described herein have been tested using virtual and physical assessment procedures. Three myoelectric control architectures were compared in a study using a physical assessment (experiment A) and a virtual assessment (experiment B). The experimental setup consisted of a three-site EMG acquisition system and a laptop running a custom application (written using LabView, National Instruments, Inc.). The latter processed the EMG signals, implemented the myoelectric control system algorithms (i.e., generated control commands as outputs) and stored the data for off-line analysis. The outputs of the myoelectric controllers were physically implemented by a multi-grasp artificial hand, connected to the laptop (during experiment A) or a virtual hand displayed on the laptop screen (during experiment B).

The EMG signals were acquired using two surface electrodes targeting the flexor digitorum superficialis (F) and extensor digitorum (E) and a third surface electrode targeting extensor carpi ulnaris (U) muscles when necessary. Self-adhesive snap electrode pairs with 2 cm inter-electrode spacing were used. A Noraxon Telemyo 2400R system sampled the EMG signals (3 kHz) while a data acquisition board (NI-USB 6211) connected to the laptop digitized them. These signals were processed using standard techniques (band pass 10-450 Hz, rectification, moving average) and were used to produce control commands based on the specific myoelectric control system. Individual EMG gains, thresholds, and offsets could be tuned for each subject.

Each of the three myoelectric control systems had a unique architecture while all other parameters including the temporal coordination and the closing time of the fingers were standardized in order to ensure a robust comparison. In particular, the three myoelectric control systems were able to map EMG signals into the identical six target postures, and hand flat (Table 2). The six postures comprised functional postures and grasps used in activities of daily living.

TABLE 2

Target postures included in each myoelectric control systems

| Target Postures | Acronym | Target Postures | Acronym |
|---|---|---|---|
| Palmar prehension | PP | Pointer | PT |
| Lateral prehension | LP | Hook | HK |
| Tip prehension | TP | Opposition | OP |
| Hand flat | HF | | |

Controller 1: Commercially Available Finite-State Machine

Controller 1 (C1) replicated the finite state machine implemented in a commercially available device: the iLIMB prosthetic hand (Touch Bionics, ltd. Livingstone, UK). This type of state machine is typical among available commercial prostheses. The architecture consisted of six states corresponding to the six target postures, not including HF. A trigger (T) iteratively changed states in a specified order. The trigger allowed for a progression in the sequence of states in a single direction. The trigger command occurred when both EMG signals (F, E) supersede a tuned threshold (a brief co-contraction). An audible beep was provided by the experimental apparatus to indicate that a trigger command was recognized (like in the iLIMB prosthetic hand). Once inside a state, the magnitude of the difference between F and E was proportional to the speed of the hand and the sign of the difference corresponded to the opening/closing of the hand (a velocity control scheme). The fully closed posture of each state coincided to one of the target postures while the fully opened posture coincided to hand flat (HF) (full extension of all digits). Therefore, the only available postures within a state were a linear combination of the corresponding target posture and HF.

Controller 2: Vanderbilt University Controller

Controller 2 (C2) replicated a Multigrasp Myoelectric Controller developed at Vanderbilt University. The architecture consisted of two states (opposition and reposition) with multiple target postures within each state. The two states were distinguished by the abduction position of the thumb: opposition and reposition. A co-contraction trigger (T) switched between the two states. The trigger command and the hand opening/closing occurred identically to C1. The sequence of postures within each state ensured that the digits closed/opened in a coordinated manner. The transition logic between postures was not reproduced exactly due to mechanical constraints of the artificial hand used in the present study. Specifically, the actuator displacement and force thresholds were not available to use in the transition logic in our study. Instead, the transitions between the states were solely dependent on the volitional EMG input signals. The hand posture when transitioning between targets was a linear combination of the two nearest target postures.

Controller 3: Postural Controller

Controller 3 (C3) was a postural controller based on various embodiments of the present invention. The architecture used EMG signals like a joystick to morph the hand posture. As described previously, the EMG signals are mapped into two control parameters that can be represented by a coordinate in the PC domain. All locations in the PC domain corresponded to a hand posture. In this work, the three EMG signals were mapped in a radial fashion about the origin of the PC domain. The vector summation of the RMS EMG values equaled the coordinate position in the PC domain. A position control scheme was used where quiescent EMG signals corresponded to the coordinate at the origin. The coordinate, $[PC_x, PC_y]$, was converted into a joint angle array, e, by a linear transform, the Joint Angle Transform (JAT, (6)). When the coordinate equaled a target posture position, the myoelectric control system reproduced the target posture identically. As the coordinate moved between two target posture positions, the myoelectric control system reproduced a linear combination of those two postures. The architecture did not include discrete states and therefore did not require a trigger signal.

$$\theta = \begin{bmatrix} \theta_1 \\ \vdots \\ \theta_6 \end{bmatrix} = JAT * \begin{bmatrix} PC_x \\ PC_y \end{bmatrix} \quad (6)$$

Experimental Methods

Seven able-bodied subjects (aged 26 years±3 years) completed two experiments (A and B) using the three myoelectric control systems. Experiment A consisted of the southampton hand assessment procedure (SHAP) using a modified Azzurra IH2 artificial hand (Prensilia Srl, Pisa, Italy) mounted onto a splint. Experiment A tested the ability of the subjects to manipulate physical objects. Experiment B instead consisted of a virtual hand posture matching task in order to test the full range of postures for each myoelectric control system. In a single (two hour) experimental session both experiments were performed using a single controller (either C1, C2, or C3) with experiment A occurring first. Three sessions were scheduled on three different days for each subject. The order of the controllers tested across the three days was randomized across subjects. All subjects claimed to have normal vision/upper limb function and were not practiced at myoelectric control. All subjects conducted the experiment using their left arm to match the handedness of the robot hand available.

Experiment A

In experiment A, the subjects performed the SHAP wearing the artificial hand. The hand was mounted on an able-bodied splint which included a handlebar so that the physiological limb would maintain an anatomically neutral position. The SHAP is a standardized hand assessment procedure that measures the hand function relative to normal able-bodied function using 26 activities of daily living tasks which span the functional grasps. It was shown to be reliable and was validated so that results of independent studies can be compared. As instructed by the SHAP protocol, subjects were asked to complete tasks consisting of the manipulation of abstract objects (cylinders, spheres, tabs, etc.) and activities of daily living (turning a door handle, picking up coins, moving containers, lifting a tray, etc.). The 26 tasks were performed as quickly as possible and were self-timed by the subject. The duration of each task was used to calculate a SHAP score which described the overall function of the subject. Since the SHAP used a time-based protocol, the best performance equated to the fastest performance across all tasks.

The artificial hand used during the SHAP was a modified IH2 Azzurra hand. The unmodified version of this hand consists of five underactuated digits (two joints per digit) driven by five motors which actuated the flexion/extension of the thumb, index, middle, ring/little as a pair and the ab/adduction of the thumb. The hand was modified in order to improve grasp stability during tip prehension and lateral prehension. In particular the thumb and index fingers were splinted so that they became a single jointed digit about the metacarpophalangeal joint and compliant material was added to the fingertips.

Before the experiment, the EMG control sites were located by palpating the forearm and the electrodes were fixed. Then the splint with the robot hand was fitted to the subjects' forearm using adjustable straps in an anatomically correct position. The EMGs thresholds, offsets, and gains were tuned as the subject suspended the hand and splint in order to best compensate for the nominal EMG activity due to the weight of the system.

During the experiment subjects sat in an upright position in front of a table where the SHAP materials were placed. The subject rehearsed each SHAP task until he/she was able to reliably perform it as suggested by the SHAP assessor's manual. The subject performed the task until satisfied that the fastest possible time was achieved. Five tasks of the original SHAP were not included in our study (button board, food cutting, rotate key, zipper, and screwdriver tasks) due to mechanical limitations of the hand available and were given the maximum time, 100 seconds, as prescribed by the SHAP assessor's manual. Subjects were instructed to rest between SHAP tasks as needed.

Experiment B

In experiment B, the subjects performed a virtual hand posture matching task by controlling the movements of a virtual hand (VH) displayed on the laptop using the same EMG control sites as in experiment A. The virtual hand had the same physical architecture of the IH2 Azzurra hand and responded in real-time to the output of the myoelectric control systems. During the experiment subjects sat in an upright position in front of the laptop (the splint and the robot hand were not used). The subjects were asked to match the posture of the virtual hand to one out of six target postures as quickly as possible. The target posture was displayed as a static image of the virtual hand in the appropriate position. A successful trial consisted of matching the virtual hand to the target posture in ten seconds or less (including a one second hold time) otherwise the trial was considered a failure. The virtual hand matched the target posture when the coordinate was within the 14% radii of the target position in the PC domain and was indicated by the visual interface. The experiment consisted of 60 trials (10 attempts at each target posture). The sequence of target postures was randomized across subjects. Before experiment B the EMG acquisition was retuned. The virtual hand task tested the ability of each subject to produce the specified target postures as opposed to the SHAP which required the completion of the task and not a specific posture.

Performance Metrics

In experiment A, the SHAP Score ($S_S$) was used as one of the performance metrics. The $S_S$ was designed to measure a subject's artificial hand function and was derived from the time to complete the SHAP tasks; a score of 100 corresponded to normal, able-bodied hand function while a score of 0 equated to minimal function. A SHAP Deviation ($S_D$) which is the percent difference from the subject average $S_S$ as described by equation (7) where n is the subject and c is the myoelectric control system. Positive $S_D$ occurs when the $S_S$ for the myoelectric control system is greater than the subject's average and vice versa.

$$S_D^c = \frac{\sum_{n=1}^{7}\left(\frac{S_S^{n,c}}{\sum_{c=1}^{3} S_S^{n,c}/3} - 1\right)}{7} * 100 \qquad (7)$$

In experiment B, several metrics were used to quantify the performance. The completion rate (CR) is the number of successful trials per total number of trials. The movement time (MT) is the duration of successful trials in seconds not including the one second hold time. The average EMG amplitude (EMG AMP) is a measure of effort based on the RMS of the EMG activity from each electrode for each trial and is calculated as the percent difference from the subject average as sorted by controller (c, (8)) or by controller and target posture (p,(9)). Positive AMP occurs when the subject produces more EMG activity (i.e.—effort) for a controller/posture than the subject average and vice versa. EMG AMP was only calculated for experiment B since the manipulation tasks in experiment A caused compensatory EMG activity which were not of interest.

$$AMP_c = \left(\frac{\text{RMS Average}_c}{\text{Subject RMS Average}} - 1\right) * 100 \qquad (8)$$

$$AMP_{c,p} = \left(\frac{\text{RMS Average}_{c,p}}{\text{Subject RMS Average}} - 1\right) * 100 \qquad (9)$$

Better performance in experiment B was quantified by higher CR, lower MT, and lower EMG AMP. One-factor ANOVA's were used throughout and Bonferroni post-hoc corrections for multiple comparisons were used when applicable with a significance level of 0.05. Experimental results report means±standard error of the mean.

Results—Experiment A

The $S_S$'s for each controller were equal to 38±2.5, 41±1.9, and 45±1.0 for C1, C2, and C3 respectively. The $S_S$'s were not significantly different across myoelectric control systems (p=0.08). However, the average $S_S$ for each subject ranged from 35 to 48 and was found to be significantly different (p<0.05, not shown). In other words, some subjects were more proficient at the SHAP than others irrespective of the controller. Therefore, the $S_D$ was used since it normalized the $S_S$ to the subject average. The mean $S_D$'s across subjects were equal to −8.0%±2.6%, −0.6%±1.6%, and 8.6%±2.2% for C1, C2, and C3 respectively. Post-hoc analysis found that the $S_D$ for C3 was significantly greater than both C1 and C2 (p<0.001, p<0.05) thereby suggesting that on average subjects performed the activities of daily living more proficiently using C3 than C1 or C2.

Results—Experiment B

The completion rates equaled to 97%±1.4%, 99%±0.3%, and 86%±2.9% for C1, C2, and C3 respectively. Post-hoc analysis found that the CR for C3 was significantly less than both C1 and C2 (p<0.01, p<0.001 respectively). The movement times equaled 3.9 s±0.3 s, 3.3 s±0.2 s, and 2.7 s±0.4 s for C1, C2, and C3 respectively. There was no significant difference between the three controllers (p=0.06), however there was strong trend where the MT decreased from C1 to C2 to C3. The EMG AMP equaled 25%±24%, −1%±26%, and −24%±13% for C1, C2, and C3 respectively. There was no significant difference between the three controllers (p=0.31), however there was a trend where the EMG AMP decreased from C1 to C2 to C3. To summarize, C3 was the least accurate controller in reproducing the six target postures, however tended to be the fastest and least effortful controller.

The same results were sorted by target posture in order to analyze the intricacies of the PC architecture used in C3. In C3, the target postures that require the activation of a single EMG site (PP, TP, and LP) are considered 1 degree of freedom (DoF) targets. The 2-DoF targets postures (HK, PT, and OP) are acquired by activating two EMG (i.e.—a co-contraction). All target postures in C1 and C2 are considered 1-DoF since none require co-contraction. The CR for the 1-DoF trials equaled 97%±1.4%, 99%±0.3%, 96%±2.2% for C1, C2, and C3 respectively. There was no difference in CR between the controllers for the 1-DoF trials (p=0.40). However, the CR for C3 2-DoF trials equaled 78%±4.2% and was significantly different (p<0.001) than the 1-DoF trials. In other words, the failed attempts when using C3 occurred almost exclusively when the target posture required a co-contraction (a 2-DoF target). The MT for the 1-DoF trials equaled 3.9 s±0.3 s, 3.3 s±0.2 s, and 1.9 s±0.4 s for C1, C2, and C3 respectively and the MT for the 2-DoF C3 trials equaled 3.8 s±0.4 s. The MT for the C3 1-DoF trials was significantly less than the MT for the C1, C2, and C3 2-DoF trials (p<0.001). The EMG AMP for the 1-DoF trials equaled 25%±24%, −1%±26%, and −34%±11% for C1, C2, and C3 respectively, and the EMG AMP for the C3 2-DoF trials equaled −15%±15%. There was no significant difference between EMG AMP for the 1-DoF or 2-DoF trials (p=0.24) however there was a trend where the EMG AMP decreased from C1 to C2 to C3 2-DoF trials to C3 1-DoF trials. In general, the C3 1-DoF trials were equally accurate, faster, and tended to be less effortful than C1 and C2. On the contrary, the C3 2-DoF trials were less accurate, equally timely, and were equally effortful as C1 and C2.

Further sorting was performed in order to provide insight into the different EMG AMP required to produce the target postures within each myoelectric control system. It is worth recalling that a zero EMG AMP occurred when the posture required the average EMG activity for the subject. For C1 the EMG AMP monotonically increases from the initial target posture (TP) to the most distant one (OP). This finding is logical since a trigger command is required to sequentially move between states and thereby increases the required effort to reach the more distant target postures. For C2, the EMG AMP is significantly greater (p<0.001) for target postures in the opposition state (OP, TP, and PP) than for the reposition state (PT, HK, and LP). Since the hand posture in experiment A was initialized to the HF state for all trials and myoelectric control systems, the opposition state in C2 required an extra trigger command (more EMG activity) to switch from the reposition state. For C3, the EMG AMP is significantly greater (p<0.001) for the 2-DoF target postures (HK, OP, and PT) than for the 1-DoF target postures (PP, TP, and LP). This is a logical finding since modulation of two control sites (a co-contraction) is a more effortful task. While the controllers were equally effortful on average, the effort for each target posture differed significantly within each control architecture.

Discussion

Significantly different results from both the virtual and physical assessment procedures were found. An asset of the present study was that it allowed for comparisons between myoelectric control systems due to the standardized experimental design where the same interface and hardware was used for all conditions.

In experiment A, C3 was shown to be the best performing architecture as described by $S_D$. The trigger command used in C1 and C2, but not in C3, inherently retarded the completion of the activity of daily living. Subjects were observed producing the trigger command during the reaching phase of the activity of daily living in order to complete the task as quickly as possible when using C1 and C2. The absence of a trigger command in C3 proved to be advantageous. This finding supported a similar study in which pattern recognition (without trigger commands) and state machine myoelectric control systems were compared. Furthermore, the architectures of C1 and C2 required extension EMG activity in order to release an object whereas C3 required quiescent EMG activity (i.e.—minimal activity). These traits resulted from the velocity control scheme in C1 and C2 compared to the position control scheme in C3. A velocity control scheme deciphered EMG activity as a speed and direction of hand movement and therefore quiescent EMG activity equated to no hand movement. EMG activity was necessary to close and open the hand. A position control scheme deciphered EMG activity as a position within the architecture. In C3, EMG activity was only necessary to close the hand; the hand opened when quiescent EMG activity was detected. However, the position control scheme in C3 required continual EMG activity in order to maintain a grasp. This fact could cause fatigue (although not noticed here) and might need to be mitigated with switches or other logic within C3. In general, the need for extension activity in order to release an object in C1 and C2 slowed the completion of the tasks compared to C3.

In experiment B, C3 was the least accurate (lowest CR) controller. We found that the dimensionality of the architectures affected the accurate reproduction of target postures. More specifically, the state machine architectures used in C1 and C2 restricted the subject to a linear arrangement of states, and therefore the posture matching task only required the modulation of one EMG signal at a time. The PC architecture used in C3 presented the same postures in a planar, two-dimensional arrangement. Thereby, half of the target postures required the modulation of one EMG signal (1-DoF) and half required the modulation of two EMG signals (2-DoF) in order to reproduce the target posture. The added dimension of the PC architecture in C3 (i.e. the need for co-contractions) negatively affected the CR of the myoelectric control system. These results supported our previous findings that described a reduction in CR with an increase in dimensionality. These results indicate that clinically viable myoelectric control systems should be simple with one EMG signal active at a time.

The MT metric in experiment B described the same trend seen in the $S_S$ in experiment A. The movement time tended to decrease from C1 to C2 to C3 which mirrored the $S_S$ and $S_D$ metrics. Furthermore, the movement time for the C3-1DoF trials were significantly faster than the other controllers. The similar trend between the $S_S$ and the movement time metric was logical since both are time-based metrics. This trend supported the fact that both the physical and virtual assessment protocols limited confounding variables and therefore produced similar result across assessment techniques.

The EMG AMP metric described the relative effort required for each controller/posture. While the controllers required equal effort on average, the effort for each target posture differed significantly and was dependent on the controller architecture. In general, the sequential arrangement of states in C1 caused the closer postures to the initial position to be achieved more easily. Similarly in C2, the postures within the initial state (HF state) were achieved more easily than the postures not in the initial state (OP state). In C3, the EMG AMP metric highlighted the difficulty of commanding the 2-DoF target postures compared to the 1-DoF target postures. It should be noted that the EMG AMP metric was biased by experimental design. More specifically, the initial posture/state within each controller was the same for all trials in experiment B to ensure a standardized methodology across controllers. The reordering of states within C1 and/or the rearrangement of postures in the PC domain in C3 would have caused the EMG AMP values to differ for the specific postures. However, we concluded that the general insights still hold for all of the controllers; the effort increased with the number of trigger commands required in C1 and C2 and the 2-DoF postures in C3 required more effort than the 1-DoF postures.

The clinical implementation of the three controllers is feasible today. The EMG acquisition and processing was performed using clinically available hardware and standard processing techniques. Several five motor prosthetic hands are available today, and six motor devices are becoming available. A clinical consideration when implementing the state-machine architectures (C1 and C2) is the design of the trigger signal. This work implemented the same trigger design for both C1 and C2, however more complex trigger designs including hold open, double impulse, and/or triple impulse are clinically available. In general, the trigger design must balance the ease of use for the subject with the reliability of the trigger signal. Subject over-exertion and/or false triggers should be minimized in order to maintain a high quality control interface when using state-machine architectures. A clinical consideration when implementing the PC architecture (C3) is the availability of three independent surface EMG sites on the residual limb of persons with transradial amputation. Three control sites are preferable to two in order to span the entire PC domain using a radial mapping of EMG signals in the PC domain.

Exemplary Computer System Overview

Embodiments of the present invention include various steps and operations, which have been described above. A variety of these steps and operations may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 10 is an example of a computer system 1000 with which embodiments of the present invention may be utilized. According to the present example, the computer system includes a bus 1010, at least one processor 1020, at least one communication port 1030, a main memory 1040, a removable storage media 1050, a read only memory 1060, and a mass storage 1070.

Processor(s) 1020 can be any known processor, such as, but not limited to, Intel® lines of processors; AMD® lines of processors; or Motorola® lines of processors. Communication port(s) 1030 can be any of an RS-232 port for use with a modem-based dialup connection, a 10/100 Ethernet port, or a Gigabit port using copper or fiber. Communication port(s) 1030 may be chosen depending on a network such as a Local Area Network (LAN), Wide Area Network (WAN), or any network to which the computer system 1000 connects.

Main memory 1040 can be Random Access Memory (RAM) or any other dynamic storage device(s) commonly known in the art. Read only memory 1060 can be any static storage device(s) such as Programmable Read Only Memory (PROM) chips for storing static information such as instructions for processor 1020.

Mass storage 1070 can be used to store information and instructions. For example, hard disks such as the Adaptec® family of SCSI drives, an optical disc, an array of disks such as RAID, such as the Adaptec family of RAID drives, or any other mass storage devices may be used.

Bus 1010 communicatively couples processor(s) 1020 with the other memory, storage and communication blocks. Bus 1010 can be a PCI/PCI-X or SCSI based system bus depending on the storage devices used.

Removable storage media 1050 can be any kind of external hard-drives, floppy drives, IOMEGA® Zip Drives, Compact Disc-Read Only Memory (CD-ROM), Compact Disc-Re-Writable (CD-RW), and/or Digital Video Disk-Read Only Memory (DVD-ROM).

The components described above are meant to exemplify some types of possibilities. In no way should the aforementioned examples limit the scope of the invention, as they are only exemplary embodiments.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates the various aspects of the invention in any number of claim forms. For example, while only one aspect of the invention is recited as a computer-readable medium claim, other aspects may likewise be embodied as a computer-readable medium claim, or in other forms, such as being embodied in a means-plus-function claim. (Any claims intended to be treated under 35 U.S.C. § 112, ¶6 will begin with the words "means for", but use of the term "for" in any other context is not intended to invoke treatment under 35 U.S.C. § 112, ¶6.) Accordingly, the applicant reserves the right to pursue additional claims after filing this application to pursue such additional claim forms, in either this application or in a continuing application.

What is claimed is:

1. A postural controller for dynamically creating custom positions of a prosthetic device based on muscular contractions of a user, the postural controller comprising:
   a processor;
   a memory having stored thereon a postural control space having a set of pre-selected postures each created by a unique set of multiple, pre-defined joint angles of the prosthetic device to achieve each of the pre-selected postures,
      wherein each pre-selected posture in the set of pre-selected postures is located at a different position than any other pre-selected posture within the postural control space; and
      wherein the prosthetic device includes a prosthetic hand or a robotic hand and the set of pre-selected postures within the postural control space include tripod, key grip, and power grip;
   the memory also having stored thereon instructions that when executed by the processor cause the postural controller to:
      receive processed EMG signals representing muscular contractions of the user of the prosthetic device; and
      map the processed EMG signals to a point in the postural control space using the processor,
         wherein the processed EMG signals are mapped to the point in the postural control space based, at least in part, on a time-varying resultant vector of the processed EMG signals;
         wherein the point in the postural control space lies between two of the pre-selected postures indicating a blended posture desired by the user while the processed EMG signals are mapped to the point in the postural control space; and
         wherein the blended posture is a custom combination based on proximity of the point to the two pre-selected postures the point lies between; and
      transform the point in the postural control space into a set of desired joint angles by morphing the joint angles of the two of the pre-selected postures that the point lies between in the postural control space.

2. The postural controller of claim 1, wherein the postural controller is communicably coupled to a feedback controller that will position the prosthetic hand or the robotic hand into the blended posture desired by the user.

3. The postural controller of claim 1, wherein the instructions when executed by the processor further cause the postural controller to generate control signals to cause a set of actuators to set the joint angles of the prosthetic device to the set of desired joint angles.

4. The postural controller of claim 3, wherein to generate the control signals, the postural controller uses signals generated from an encoder or from a pressure sensor to generate the control signals.

5. The postural controller of claim 1, wherein the postural control space includes attractive regions around the pre-selected postures and wherein the instructions will further cause the postural controller to determine whether the point lies within the attractive regions and, upon detection that the point lies within a first attractive region of the attractive regions, select the set of multiple joint angles as the pre-selected posture surrounded by the first attractive region without continued muscular contractions from the user.

6. The postural controller of claim 1, wherein the postural control space can be defined through a graphical user interface.

7. The postural controller of claim 1, wherein the instructions that when executed by the processor further cause the postural controller to:
   measure baseline EMG signals from muscular contractions performed in different orientations of the prosthetic device;
   receive a live set of EMG signals representing the muscular contractions; and
   generate the processed EMG signals by applying a filtering or dynamically tuning the live set of EMG signals in view of the baseline EMG signals.

8. The postural controller of claim 1, wherein the instructions when executed by the processor further cause the postural controller to communication with a feedback controller to generate control signals to cause a set of actuators to set the joint angles of the prosthetic device to the set of desired joint angles so that the blended posture is created by the prosthetic device as long as the processed EMG signals map to the point in the postural control space and as the point in the postural control space moves to a new location in the postural control space, the blended posture is dynamically recomputed to identify an updated blended posture corresponding to an updated blended set of multiple joint angles based on the new location of the point in the postural control space.

9. The postural controller of claim 1, further comprising a conversion module configured to use a vector summation algorithm to map the processed EMG signals to the point in the postural control space by computing directional vectors from the processed EMG signals based on positions of electrodes on a limb of a patient.

10. The postural controller of claim 9, wherein the electrodes include a first set of electrodes on a dorsal side of the limb corresponding to an x-axis in the postural control space and a second set of electrodes on a medial side of the limb corresponding to a y-axis of the postural control space.

11. The postural controller of claim 1, further comprising:
   means for monitoring muscular contractions and generating EMG signals;
   means for generating the processed EMG signals by removing noise from the EMG signals; and
   means for dynamically tuning the processed EMG signals based on an orientation of the prosthetic device.

* * * * *